(12) United States Patent
Morrissey

(10) Patent No.: US 7,790,176 B2
(45) Date of Patent: Sep. 7, 2010

(54) FORMULA FOR IMPROVING PHYSICAL PERFORMANCE AND RELATED METHODS

(75) Inventor: Edward Stephen Morrissey, Ojai, CA (US)

(73) Assignee: Botanica BioScience Corporation, Ojai, CA (US)

( * ) Notice: Subject to any disclaimer, the term of this patent is extended or adjusted under 35 U.S.C. 154(b) by 153 days.

(21) Appl. No.: 12/154,844

(22) Filed: May 27, 2008

(65) Prior Publication Data

US 2008/0299145 A1 Dec. 4, 2008

Related U.S. Application Data

(60) Provisional application No. 60/932,709, filed on Jun. 1, 2007.

(51) Int. Cl.
*A61K 36/06* (2006.01)
*A61K 36/752* (2006.01)
*A61K 36/00* (2006.01)

(52) U.S. Cl. .................. 424/195.15; 424/736; 424/725

(58) Field of Classification Search ........................ None
See application file for complete search history.

(56) References Cited

U.S. PATENT DOCUMENTS

| 6,024,984 A | * | 2/2000 | Hanawa et al. | 424/520 |
| 2003/0219500 A1 | * | 11/2003 | Howard et al. | 424/729 |
| 2006/0292251 A1 | * | 12/2006 | Lin et al. | 424/757 |
| 2007/0026511 A1 | * | 2/2007 | Morrissey et al. | 435/190 |

FOREIGN PATENT DOCUMENTS

| CN | 1087270 | * | 6/1994 |
| CN | 1245703 | * | 3/2000 |
| CN | 1254592 | * | 5/2000 |
| CN | 1374011 | * | 10/2002 |

OTHER PUBLICATIONS

Burke, E. Nutrition Science Report. Oct. 1999. 4 pages.*

* cited by examiner

*Primary Examiner*—Christopher R. Tate
(74) *Attorney, Agent, or Firm*—McKinney Law Group; Jeffrey A. McKinney

(57) ABSTRACT

The present invention generally relates to the use of a formula that improves human and animal endurance, stamina, performance and other physical parameters. In one composition aspect, the formula or composition of the present invention includes a *Flammulina velutipes* extract and citrus peel.

7 Claims, 4 Drawing Sheets

FORMULA FOR IMPROVING PHYSICAL PERFORMANCE AND RELATED METHODS

This application claims priority to U.S. Prov. Appl. No. 60/932,709, filed Jun. 1, 2007, under 35 U.S.C. 119, which is hereby incorporated-by-reference for all purposes.

FIELD OF THE INVENTION

The present invention generally relates to the use of a formula that improves human and animal endurance, stamina, performance and other physical parameters.

BACKGROUND OF THE INVENTION

There have been a number of reported formulations containing *Flammulina velutipes*. For example, a product with the name "2<sup>nd</sup> Wind" was sold briefly as an athletic recovery formula. The product included six powdered ingredients, some of which were based on three types of non-extracted, powdered mushrooms; *Flammulina velutipes* mycelium accounted for 50% of the formula. The six ingredients were: *Flammulina velutipes*; Eleuthero root; Reishi; Citrus peel; Ginseng root; and, *Cordyceps sinensis*.

U.S. Pat. Appl. 20070026511 to Morrissey discusses an improved composition including a *Flammulina velutipes* extract. The extract has the following characteristics: a moisture content ranging from 0% to 40%; a protein content ranging from 20% to 40%; a carbohydrate content ranging from 40% to 80%; an ash content ranging from 0% to 15%; and, a fat content ranging from 0% to 5%. Animal studies of the extract showed it exhibited significantly and substantially improved activity vis-à-vis 2<sup>nd</sup> Wind.

Despite improvements in performance-enhancing compositions and methods, there is a need in the art for new formulae and methods. Providing such formulae and methods is one object of the present invention.

SUMMARY OF THE INVENTION

The present invention generally relates to the use of a formula that improves human and animal endurance, stamina, performance and other physical parameters.

In a composition aspect, the formula or composition of the present invention includes a *Flammulina velutipes* extract and citrus peel.

In another composition aspect, the formula or composition of the present invention includes a *Flammulina velutipes* extract and astragalus root.

In another composition aspect, the formula or composition of the present invention includes a *Flammulina velutipes* extract and a stimulant.

In another composition aspect, the formula or composition of the present invention includes a *Flammulina velutipes* extract, citrus peel, and astragalus root.

In another composition aspect, the formula or composition of the present invention includes a *Flammulina velutipes* extract, astragalus root, and a stimulant.

In another composition aspect, the formula or composition of the present invention includes a *Flammulina velutipes* extract, citrus peel, astragalus root, and a stimulant.

In a method aspect, the method of the present invention includes supplying a composition of the present invention to a human or animal to obtain one or more of the following in the human or animal: endurance improvement; stamina improvement; performance improvement; energy improvement; recovery improvement; soreness reduction; fatigue reduction; muscle degradation reduction; serum urea concentration reduction; liver glycogen storage improvement; and, lactic acid clearance improvement.

In a kit aspect, the kit of the present invention includes a composition of the present invention, a container for holding the composition, and instructions for using the composition to obtain one or more of the following in a human or animal: endurance improvement; stamina improvement; performance improvement; energy improvement; recovery improvement; soreness reduction; fatigue reduction; muscle degradation; serum urea concentration reduction; liver glycogen storage improvement; and, lactic acid clearance improvement.

DETAILED DESCRIPTION OF THE INVENTION

Figure 1:
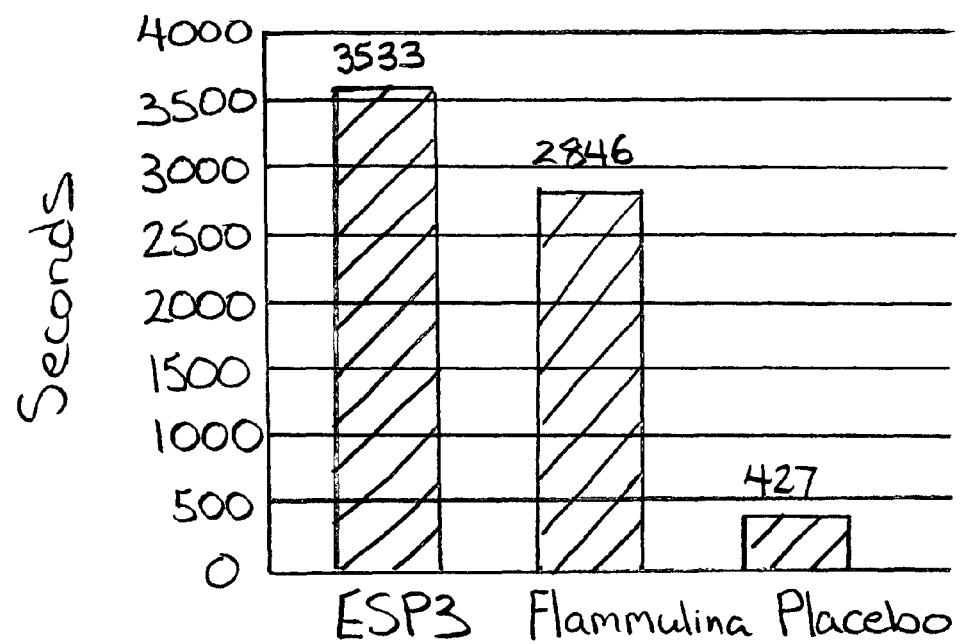
FIG. 1 shows a graphical representation of data related to a "swim time to exhaustion" test described in Example 1.
Figure 2:
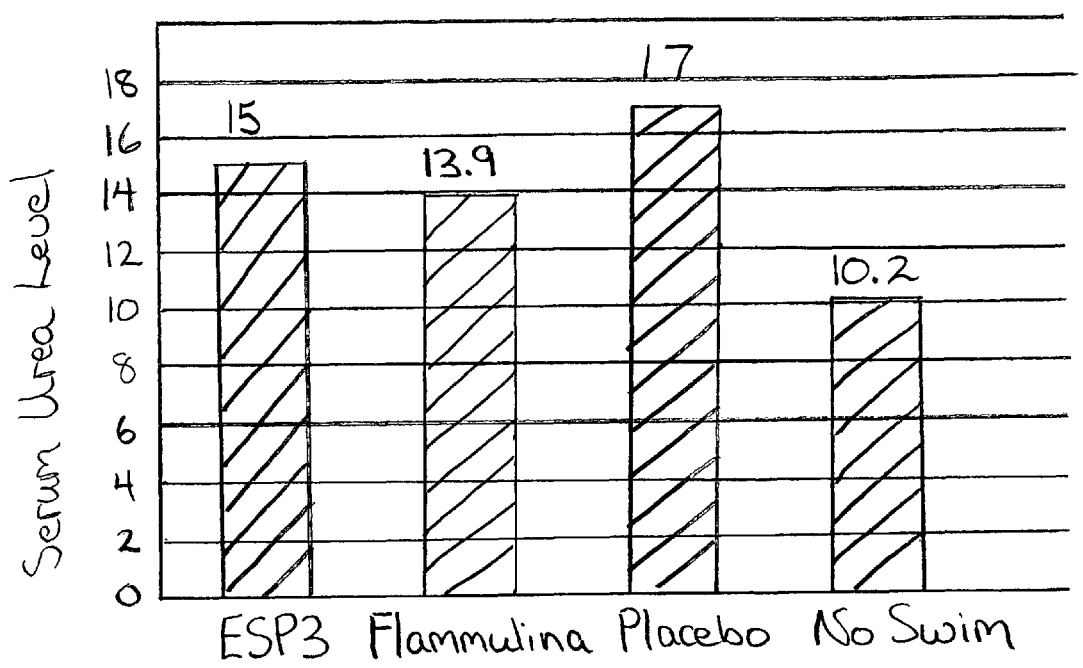
FIG. 2 shows a graphical representation of data related to a "serum urea" test described in Example 2.

The present invention generally relates to the use of a formula that improves human and animal endurance, stamina, performance and other physical parameters.

The formulation of the present invention comprises *Flammulina velutipes* extract and one or more of the following ingredients: citrus peel; astragalus root; and, a stimulant. Non-limiting examples of citrus peel include tangerine peel, orange peel, grapefruit peel, lemon peel and lime peel. Non-limiting examples of stimulants include green tea, black tea, coffee, cola nut, cocao, guarana or mate. The stimulants may include theanine, caffeine, thiophylline or another xanthine derivative.

The formulation of the present invention can stand alone as a complete product for enhancing physical performance, or it may be included as a compound ingredient in other products. Non-limiting examples of other products include food, medicine, sports beverages, meal replacement drinks, powders, dietary supplement capsules, tablets, or a simple water additive.

The formulation can be prepared in a variety of forms. Non-limiting examples of such forms include capsules, caplets, tablets, pills, dispersions, suspensions, solutions, powders, teas, syrup concentrates, bars, and chews. It can further be packaged in bottles or other packaging for sale.

Where the formulation is prepared as a capsule, it comprises at least one additional ingredient from the following list: flour; starch; modified starch; maltodextrin; cellulose; modified cellulose; protein hydrolysate; rice powder; whey powder; calcium phosphate; calcium carbonate; lactose; saccharides; sorbitol; mannitol; xylitol; stearic acid; stearate; silica; silicate; polyethylene glycol; flavors; and, colors.

Where the formulation is prepared as a tablet, it comprises at least one additional ingredient from the following list: starch; modified starch; maltodextrin; cellulose; methylcellulose; ethylcellulose; hydroxypropylmethylcellulose; modified cellulose; protein hydrolysate; rice powder; whey powder; calcium phosphate; calcium carbonate; lactose; sweeteners; sorbitol; mannitol; xylitol; zein; saccharides;

stearic acid; stearate; silica; silicate; polyethylene glycol; pharmaceutical glaze; wax; flavors; and colors.

Where the formulation is prepared as a powdered drink mix, it comprises at least one additional ingredient from the following list: starch; modified starch; maltodextrin; cellulose; modified cellulose; protein hydrolysate; whey powder; calcium phosphate; calcium carbonate; lactose; sorbitol; mannitol; xylitol; sweeteners; stearic acid; stearate; silica; silicate; flavors; and, colors.

Where the formulation is prepared as a ready-to-drink beverage, it comprises at least one additional ingredient from the following list: starch; modified starch; maltodextrin; cellulose; modified cellulose; protein hydrolysate; whey powder; calcium phosphate; calcium carbonate; lecithin; sweeteners; sorbitol; mannitol; xylitol; silica; silicate; solvents; acidifiers; citrate; preservatives; caffeine; flavors; and, colors.

Where the formulation is prepared as a semisolid, it comprises at least one additional ingredient from the following list: starch; modified starch; maltodextrin; cellulose; modified cellulose; protein hydrolysate; whey powder; calcium phosphate; calcium carbonate; lecithin oil; partially hydrogenated oil; fat; milk; milk solids; mono- or diglycerides; polysorbates; sorbitan monostearate; sweeteners; sorbitol; mannitol; xylitol; silica; silicate; solvents; acidifiers; citrate; preservatives; flavors; and, colors.

Where the formulation is prepared as a food or supplement bar, it comprises at least one additional ingredient from the following list: flour; starch; modified starch; maltodextrin; cellulose; methylcellulose; ethylcellulose; hydroxypropylmethylcellulose; modified cellulose; protein hydrolysate; whey powder; calcium phosphate; calcium carbonate; lecithin; mono- or diglycerides; polysorbates; sorbitan monostearate binders; sweeteners; sorbitol; mannitol; xylitol; silica; silicate; solvents; acidifiers; citrate; preservatives; flavors; and, colors.

The methods of the present invention involve supplying a formula of the present invention to a human or animal (e.g., dog, cat, horse) for improvement of one or more of the following characteristics: endurance improvement; stamina improvement; performance improvement; energy improvement; recovery improvement; soreness reduction; fatigue reduction; muscle degradation reduction; serum urea concentration reduction; liver glycogen storage improvement; and, lactic acid clearance improvement.

Kits of the present invention include a formula of the present invention, a container holding the formula, and instructions on how to use the formula to improve one or more of the following characteristics in a human or animal (e.g., dog, cat, horse): endurance improvement; stamina improvement; performance improvement; energy improvement; recovery improvement; soreness reduction; fatigue reduction; muscle degradation reduction; serum urea concentration reduction; liver glycogen storage improvement; and, lactic acid clearance improvement.

The following are examples of formulae according to the present invention and are not meant to be limiting in any way.

1. A formula consisting essentially of *Flammulina velutipes* extract and citrus peel.

2. A formula consisting essentially of *Flammulina velutipes* extract and astragalus root.

3. A formula consisting essentially of *Flammulina velutipes* extract and a stimulant.

4. A formula consisting essentially of *Flammulina velutipes* extract and tangerine peel.

5. A formula consisting essentially of *Flammulina velutipes* extract and orange peel.

6. A formula consisting essentially of *Flammulina velutipes* extract and grapefruit peel.

7. A formula consisting essentially of *Flammulina velutipes* extract and lemon peel.

8. A formula consisting essentially of *Flammulina velutipes* extract and lime peel.

9. A formula consisting essentially of *Flammulina velutipes* extract and green tea.

10. A formula consisting essentially of *Flammulina velutipes* extract and black tea.

11. A formula consisting essentially of *Flammulina velutipes* extract and coffee.

12. A formula consisting essentially of *Flammulina velutipes* extract and cola nut.

13. A formula consisting essentially of *Flammulina velutipes* extract and cacao.

14. A formula consisting essentially of *Flammulina velutipes* extract and guarana.

15. A formula consisting essentially of *Flammulina velutipes* extract and mate.

16. A formula consisting essentially of *Flammulina velutipes* extract, citrus peel and astragalus root.

17. A formula consisting essentially of *Flammulina velutipes* extract, tangerine peel and astragalus root.

18. A formula consisting essentially of *Flammulina velutipes* extract, orange peel and astragalus root.

19. A formula consisting essentially of *Flammulina velutipes* extract, grapefruit peel and astragalus root.

20. A formula consisting essentially of *Flammulina velutipes* extract, lemon peel and astragalus root.

21. A formula consisting essentially of *Flammulina velutipes* extract, lime peel and astragalus root.

22. A formula consisting essentially of *Flammulina velutipes* extract, citrus peel and a stimulant.

23. A formula consisting essentially of *Flammulina velutipes* extract, tangerine peel and green tea.

24. A formula consisting essentially of *Flammulina velutipes* extract, tangerine peel and black tea.

25. A formula consisting essentially of *Flammulina velutipes* extract, tangerine peel and coffee.

26. A formula consisting essentially of *Flammulina velutipes* extract, orange peel and green tea.

27. A formula consisting essentially of *Flammulina velutipes* extract, orange peel and black tea.

28. A formula consisting essentially of *Flammulina velutipes* extract, orange peel and coffee.

29. A formula consisting essentially of *Flammulina velutipes* extract, grapefruit peel and green tea.

30. A formula consisting essentially of *Flammulina velutipes* extract, grapefruit peel and black tea.

31. A formula consisting essentially of *Flammulina velutipes* extract, grapefruit peel and coffee.

32. A formula consisting essentially of *Flammulina velutipes* extract, lemon peel and green tea.

33. A formula consisting essentially of *Flammulina velutipes* extract, lemon peel and black tea.

34. A formula consisting essentially of *Flammulina velutipes* extract, lemon peel and coffee.

35. A formula consisting essentially of *Flammulina velutipes* extract, citrus peel, astragalus root, and a stimulant.

36. A formula consisting essentially of *Flammulina velutipes* extract, tangerine peel, astragalus root, and green tea.

37. A formula consisting essentially of *Flammulina velutipes* extract, tangerine peel, astragalus root, and black tea.

38. A formula consisting essentially of *Flammulina velutipes* extract, tangerine peel, astragalus root, and coffee.

39. A formula consisting essentially of *Flammulina velutipes* extract, orange peel, astragalus root, and green tea.

40. A formula consisting essentially of *Flammulina velutipes* extract, orange peel, astragalus root, and black tea.

41. A formula consisting essentially of *Flammulina velutipes* extract, orange peel, astragalus root, and coffee.

42. A formula consisting essentially of *Flammulina velutipes* extract, grapefruit peel, astragalus root, and green tea.

43. A formula consisting essentially of *Flammulina velutipes* extract, grapefruit peel, astragalus root, and black tea.

44. A formula consisting essentially of *Flammulina velutipes* extract, grapefruit peel, astragalus root, and coffee.

45. A formula consisting essentially of *Flammulina velutipes* extract, lemon peel, astragalus root, and green tea.

46. A formula consisting essentially of *Flammulina velutipes* extract, lemon peel, astragalus root, and black tea.

47. A formula consisting essentially of *Flammulina velutipes* extract, lemon peel, astragalus root, and coffee.

48. A formula consisting essentially of *Flammulina velutipes* extract, lime peel, astragalus root, and green tea.

49. A formula consisting essentially of *Flammulina velutipes* extract, lime peel, astragalus root, and black tea.

50. A formula consisting essentially of *Flammulina velutipes* extract, lime peel, astragalus root, and coffee.

The following are examples of methods according to the present invention and are not meant to be limiting in any way.

1. A method of improving endurance in a human or animal, where the method involves supplying one of formulae "1" through "50" above to a human or animal.

2. A method of improving stamina in a human or animal, where the method involves supplying one of formulae "1" through "50" above to a human or animal.

3. A method of improving performance in a human or animal, where the method involves supplying one of formulae "1" through "50" above to a human or animal.

4. A method of improving energy in a human or animal, where the method involves supplying one of formulae "1" through "50" above to a human or animal.

5. A method of improving recovery in a human or animal, where the method involves supplying one of formulae "1" through "50" above to a human or animal.

6. A method of reducing soreness in a human or animal, where the method involves supplying one of formulae "1" through "50" above to a human or animal.

7. A method of reducing fatigue in a human or animal, where the method involves supplying one of formulae "1" through "50" above to a human or animal.

8. A method of reducing muscle degradation in a human or animal, where the method involves supplying one of formulae "1" through "50" above to a human or animal.

9. A method of reducing serum urea concentration in a human or animal, where the method involves supplying one of formulae "1" through "50" above to a human or animal.

10. A method of improving liver glycogen storage in a human or animal, where the method involves supplying one of formulae "1" through "50" above to a human or animal.

11. A method of improving lactic acid clearance in a human or animal, where the method involves supplying one of formulae "1" through "50" above to a human or animal.

The following are examples of kits according to the present invention and are not meant to be limiting in any way.

1. A kit for improving endurance in a human or animal, wherein the kit includes one of formula "1" through "50" above, a container for holding the formula, and instructions for using the formula.

2. A kit for improving stamina in a human or animal, wherein the kit includes one of formula "1" through "50" above, a container for holding the formula, and instructions for using the formula.

3. A kit for improving performance in a human or animal, wherein the kit includes one of formula "1" through "50" above, a container for holding the formula, and instructions for using the formula.

4. A kit for improving energy in a human or animal, wherein the kit includes one of formula "1" through "50" above, a container for holding the formula, and instructions for using the formula.

5. A kit for improving recovery in a human or animal, wherein the kit includes one of formula "1" through "50" above, a container for holding the formula, and instructions for using the formula.

6. A kit for reducing soreness in a human or animal, wherein the kit includes one of formula "1" through "50" above, a container for holding the formula, and instructions for using the formula.

7. A kit for reducing fatigue in a human or animal, wherein the kit includes one of formula "1" through "50" above, a container for holding the formula, and instructions for using the formula.

8. A kit for reducing muscle degradation in a human or animal, wherein the kit includes one of formula "1" through "50" above, a container for holding the formula, and instructions for using the formula.

9. A kit for reducing serum urea concentration in a human or animal, wherein the kit includes one of formula "1" through "50" above, a container for holding the formula, and instructions for using the formula.

10. A kit for improving liver glycogen storage in a human or animal, wherein the kit includes one of formula "1" through "50" above, a container for holding the formula, and instruction A kit for improving endurance in a human or animal, wherein the kit includes one of formula "1" through "50" above, a container for holding the formula, and instructions for using the formula.

11. A kit for improving lactic acid clearance in a human or animal, wherein the kit includes one of formula "1" through "50" above, a container for holding the formula, and instructions for using the formula.

EXAMPLES

The following examples are presented by way of illustration, not by way of limitation.

For Examples 1-4, a formulation of *Flammulina velutipes*, tangerine peel and astragalus (ESP3) was double-blind tested for swim time (energy and stamina), lactic acid clearance (recovery), serum urea (recovery and stamina), and hepatic glycogen (energy storage, endurance). The results below show significant and strongly significant improvements over the control groups.

Example 1

FIG. 1 shows that the combination formula ESP3 improved swim time by 72% over placebo and 24% better than *Flammulina velutipes* by itself.

Example 2

ESP3 decreased serum urea by 11% compared to placebo, though slightly less than *Flammulina* on its own.

Example 3

Figure 3:
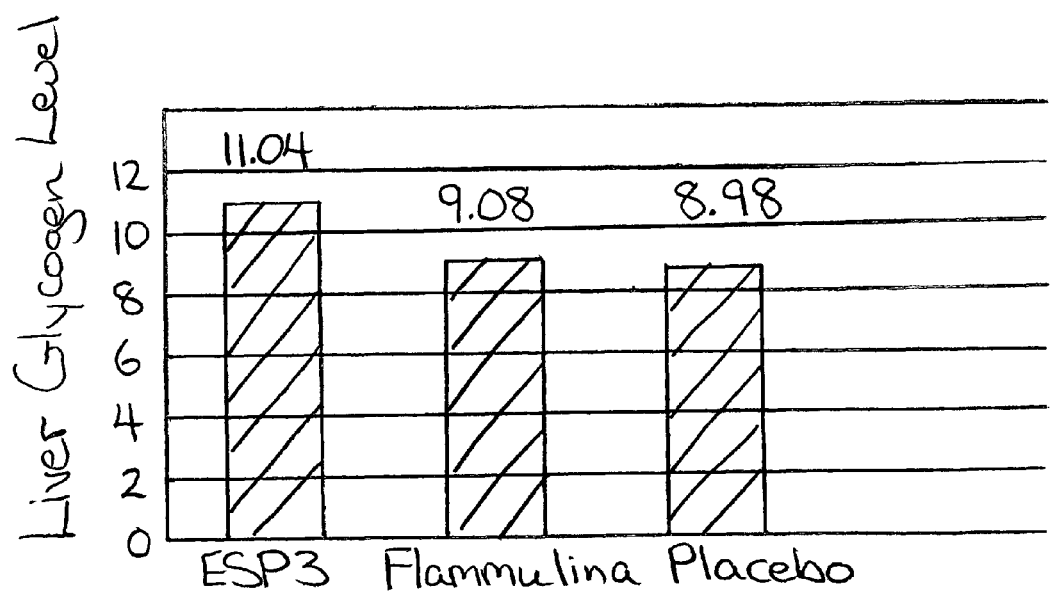
FIG. 3 shows a graphical representation of data related to a "liver glycogen after feeding" test described in Example 3.

FIG. 3 shows that ESP3 improved liver glycogen levels after feeding compared to both placebo and *Flammulina*. ESP3 increased hepatic glycogen by 23% compared to placebo.

Example 4

Figure 4:
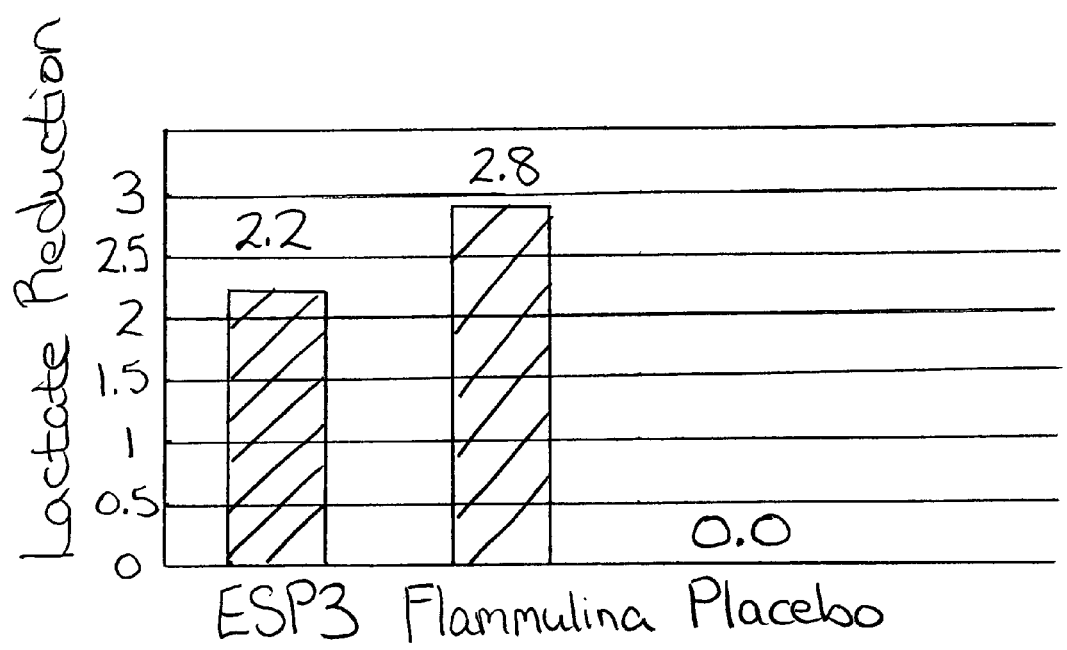
FIG. 4 shows a graphical representation of data related to a "lactate clearance during 20-minute recovery" test described in Example 4.

FIG. 4 shows that ESP3 and *Flammulina velutipes* each significantly increased lactate clearance during the recovery period, by 80% and 90% compared to placebo respectively.

The invention claimed is:

1. A composition for improving endurance or stamina consisting essentially of a *Flammulina velutipes* extract and citrus peel.

2. The composition according to claim 1, wherein the citrus peel is tangerine peel.

3. A method of improving human or animal endurance, wherein the method comprises administering an effective amount of the composition according to claim 1 to the human or animal.

4. A method for improving human or animal stamina, wherein the method comprises administering an effective amount of the composition according to claim 1 to the human or animal.

5. A method for reducing human or animal fatigue, wherein the method comprises administering an effective amount of the composition according to claim 1 to the human or animal.

6. A composition for improving endurance or stamina consisting essentially of a *Flammulina velutipes* extract, citrus peel, and astragalus root.

7. The composition according to claim 6, wherein the citrus peel is tangerine peel.

* * * * *